United States Patent
Wiek

(10) Patent No.: US 8,967,431 B2
(45) Date of Patent: Mar. 3, 2015

(54) STORAGE CONTAINER FOR THE PROVISION OF MEDIA FOR DISINFECTING, STERILIZING AND/OR MAINTAINING MEDICAL, ESPECIALLY DENTAL, INSTRUMENTS

(75) Inventor: Hans-Dieter Wiek, Hochdorf (DE)

(73) Assignee: Kaltenbach & Voigt GmbH, Biberach (DE)

( * ) Notice: Subject to any disclaimer, the term of this patent is extended or adjusted under 35 U.S.C. 154(b) by 264 days.

(21) Appl. No.: 13/576,085

(22) PCT Filed: Jan. 27, 2011

(86) PCT No.: PCT/EP2011/051124
§ 371 (c)(1),
(2), (4) Date: Sep. 5, 2012

(87) PCT Pub. No.: WO2011/101216
PCT Pub. Date: Aug. 25, 2011

(65) Prior Publication Data
US 2012/0325819 A1    Dec. 27, 2012

(30) Foreign Application Priority Data

Feb. 17, 2010  (DE) .......................... 10 2010 002 026

(51) Int. Cl.
*B65D 35/28*  (2006.01)
*A61L 2/26*  (2006.01)
(Continued)

(52) U.S. Cl.
CPC ................ *A61L 2/26* (2013.01); *A61C 19/002* (2013.01); *A61L 2/24* (2013.01); *B08B 9/00* (2013.01); *B65D 83/68* (2013.01); *B65D 83/752* (2013.01); *A61B 19/34* (2013.01)
USPC ............................ 222/95; 141/3; 222/402.16

(58) Field of Classification Search
CPC ........ B65D 83/68; B65D 83/62; B65D 83/75; B65D 83/752; A61B 19/026; A61B 19/34; A61J 11/00
USPC ........... 222/95, 94, 105, 298, 402.18, 402.16; 141/3, 10, 20, 113, 114
See application file for complete search history.

(56) References Cited

U.S. PATENT DOCUMENTS 3,788,521 A * 1/1974 Laauwe ......................... 222/94
6,196,421 B1 * 3/2001 Williams ...................... 222/129

(Continued)

FOREIGN PATENT DOCUMENTS

DE    202007000211 U1    5/2008
WO    WO-2009129902 A1    10/2009

OTHER PUBLICATIONS

International Search Report for PCT/EP2011/051124 dated May 6, 2011.

*Primary Examiner* — Lien Ngo
(74) *Attorney, Agent, or Firm* — Marshall, Gerstein & Borun LLP

(57) ABSTRACT

A device for packaging and dispensing several fluid products includes at least two sealed flexible gags arranged in a single rigid container, associated with at least one pump, the rigid container consisting of an open cylinder and the bags are provided each with a pump and a push button, and are mounted opposite on each of the two opposite openings of the cylinder. The device is applicable to appliances containing fluids to be dispensed independently of one another.

10 Claims, 1 Drawing Sheet

(51) Int. Cl.
*A61C 19/00* (2006.01)
*A61L 2/24* (2006.01)
*B08B 9/00* (2006.01)
*B65D 83/68* (2006.01)
*B65D 83/14* (2006.01)
*A61B 19/00* (2006.01)

(56) References Cited

U.S. PATENT DOCUMENTS

| | | | |
|---|---|---|---|
| 7,913,877 B2 * | 3/2011 | Neuhalfen | 222/95 |
| 2001/0025857 A1 | 10/2001 | Baudin | |
| 2005/0211724 A1 | 9/2005 | Arghyris et al. | |
| 2011/0206555 A1 * | 8/2011 | Wiek et al. | 422/28 |

* cited by examiner

STORAGE CONTAINER FOR THE PROVISION OF MEDIA FOR DISINFECTING, STERILIZING AND/OR MAINTAINING MEDICAL, ESPECIALLY DENTAL, INSTRUMENTS

BACKGROUND OF THE INVENTION

1. Field of the Invention

The present invention relates to a storage container for the provision of media, which is provided for disinfecting, sterilizing and/or maintaining medical instruments. In particular, dental instruments are to be conditioned with the media in a reconditioning device.

2. Related Technology

Medical or dental handpieces are tubular parts which the doctor holds as a handle during treatment. A handpiece conventionally used in dental practice is a so-called drill handpiece, which carries a treatment tool, in particular a drill, at its forward end and is coupled at its rear end to a supply hose by means of a coupling. Supply lines for power for driving the treatment instrument, as well as fluid lines for treatment media, for example air and/or water, extend through the handpiece. A distinction is often made between so-called turbine handpieces, in which compressed air is provided for supplying a turbine arranged in the forward end region, and so-called motor handpieces, which have an electric motor as the drive unit.

In order to maintain the function of the handpieces, maintenance, in particular of the rotatably mounted drive elements, is required from time to time. Furthermore, ever increasing hygiene demands in dental practice mean that handpieces have to be conditioned at regular intervals. Successful conditioning and compliance with the corresponding requirements must be fully documented by the dentist, which involves a not inconsiderable outlay in terms of personnel and organization.

Manual reconditioning of dental handpieces has hitherto been carried out by first disinfecting the instruments by spraying and washing them externally after use on a patient. Cleaning of the interior of the instruments, on the other hand, was generally not carried out. In the meantime, however, cleaning and disinfecting devices in which the instruments are conditioned before being subjected to maintenance with oil have become available on the market. Machine conditioning has clear advantages over manual maintenance of the instruments, because only a machine process permits reliable and reproducible cleaning and maintenance.

However, the devices known hitherto can generally be used only for individual conditioning steps, so that cleaning, maintenance and sterilization must each be carried out separately. All the devices required therefor take up a relatively large amount of space, and electrical, pneumatic and fluid connections are required for each of the devices. Consequently, the performance of a complete machine conditioning of dental instruments by means of individual devices is very laborious and is associated with a high outlay in terms of cost.

A further disadvantage is that the individual devices are generally not linked with one another, so that there can be no exchange of data between the devices. This in turn leads to extra work for the operating personnel, because it is not possible to prepare fully automatic documentation of instrument conditioning. Furthermore, the instruments must be moved manually from device to device in intermediate steps, which is associated with intensive personnel use and a large time requirement.

For the reasons mentioned above, increasing use has recently been made of devices in which all the steps for reconditioning dental instruments can be carried out. Such devices thus allow, for example, both disinfection or sterilization as well as cleaning and maintenance of the instruments. To that end, the devices are connected with various storage containers so that they can receive the active agents used during the reconditioning. For example, within the context of the reconditioning the device uses a cleaning agent, a disinfectant and a maintenance oil. These agents are conventionally available in the form of spray cans. The outlay and space required to attach the various spray cans to the device is consequently comparatively great and expensive.

SUMMARY OF THE INVENTION

The object underlying the present invention is to provide a novel arrangement to solve the problem outlined above.

The object is achieved by a storage container for the provision of media.

The solution according to the invention is based on the idea of using a storage container that contains a plurality of media simultaneously. The container is so configured that the various media can be removed individually and selectively.

Accordingly, there is proposed according to the invention a storage container for the provision of media for disinfecting, sterilizing and/or maintaining medical, especially dental, instruments, wherein the storage container is in the form of a can in which there is formed a first receiving region which is connected with a first removal element and contains a first medium, and wherein the first receiving region is in contact over at least part of its periphery with a second receiving region which contains a second medium and is connected with an attachment element for removal of the second medium and for delivery of a propellant into the second receiving region.

Accordingly, the spray can according to the invention is so configured that at least two different media are arranged in different receiving regions. The media can be removed from the can separately. The space required for attaching the storage containers for the media to the above-described system for reconditioning dental handpieces is consequently significantly reduced.

The removal element connected with the first receiving region is preferably a valve. The first receiving region can then be formed in particular by a bag.

The second receiving region likewise has an attachment element, which is preferably formed by a rubber stopper. The removal element for the first receiving region and the attachment element for the second receiving region can be arranged at two opposite ends of the can.

If the storage container according to the invention is used in a system for disinfecting, sterilizing and/or maintaining medical, especially dental, instruments, it preferably has an attachment device in the form of a needle for removal of the second medium from the storage container. The delivery of the propellant can also take place by way of the rubber stopper by means of a needle, the two needles in particular being arranged concentrically to one another. There can be used as the propellant in particular compressed air, which is provided by the system.

Ultimately, the present invention creates a storage container which in a simple manner permits the removal of various media by a system for reconditioning dental instruments.

BRIEF DESCRIPTION OF THE DRAWINGS

The invention is to be explained in greater detail below by means of the accompanying drawing, in which.

DETAILED DESCRIPTION

Figure 1:
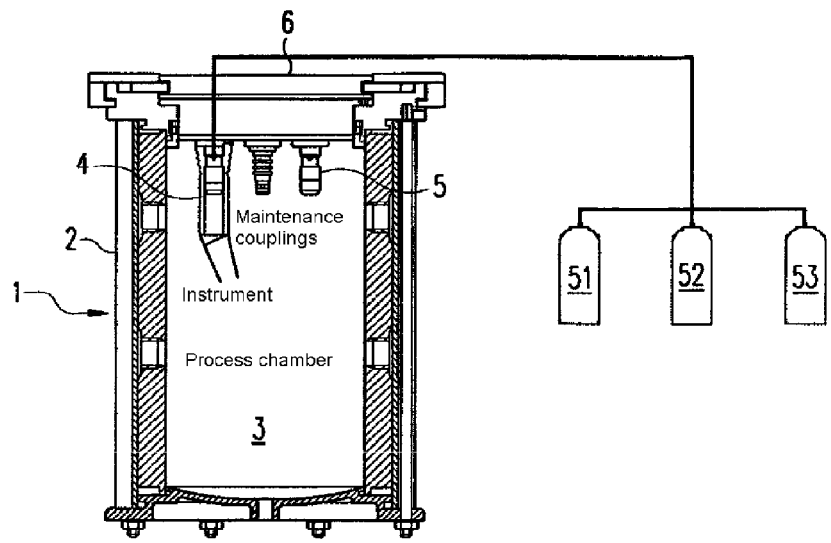
FIG. 1 shows, in a sectional view, a process or rinsing chamber of a device for disinfecting, sterilizing and/or maintaining dental instruments.

FIG. 1 first shows, in schematic form, the configuration of a device for disinfecting, sterilizing and/or maintaining medical, especially dental, instruments, the device being provided generally with the reference numeral 1 hereinbelow. The central element of the maintenance device 1 according to the invention is a pressure container 2, which encloses a process or rinsing chamber 3. The instruments 4 to be cleaned or maintained are arranged in this rinsing chamber 3 while the process is being carried out. The arrangement of the instruments 4 is effected by means of an instrument carrier, on which a plurality of plug-in positions or couplings 5 are arranged. Different couplings 5 are preferably provided, so that instruments 4 with coupling systems from different manufacturers can be conditioned. In the present case, the lid 6 of the process chamber 3 is used as the instrument carrier. This lid 6 provides the fluid coupling of the instruments 4 that are to be cleaned to a supply system. It is clamped on the rim of the pressure container 2 and sealed with respect to it by a locking device. The individual instruments 4 and their channels can then be subjected, individually or together, to a cleaning and/or maintenance agent via connecting pipes integrated into the lid 6.

The process sequence in the case of the cleaning and/or maintenance of the instruments 4 is first to be described generally hereinbelow. Before the start of the conditioning, it is checked that the process chamber 3 is pressure-tight. It is thereby ensured that the lid 6 is fitted correctly and is locked with the pressure container 2. A check is also made to ensure correct connection of the fluid lines between the lid 6 and lines running in the rim of the pressure container 2.

For the water supply to the device 1, tap water is preferably filtered by means of an osmosis system with or without downstream mixed-bed ion exchangers, the dissolved salts being removed. The water, with a quality of <15 μS/cm, is passed into a storage container on the device side, the fill level being monitored by a level switch, which is in the form of a floating switch, and the quality being monitored via a conductance sensor. For hygiene reasons, the inlet into the storage container is configured with a so-called free-fall distance.

In the conditioning of the instruments by means of the device according to the invention, the following steps are then executed in succession:

a) Cleaning

Water is first passed from the above-described storage container into the process chamber 3, it being possible for this operation to be carried out by a pump or via a vacuum by suction. In the process chamber 3, the water is heated to about 45° C. by means of heating elements. It is thereby ensured that the temperature is not above 45° C. in order to prevent the coagulation of albumin. The water is further circulated by means of a pump and directed via spray nozzles, which are attached to the lateral surface of the pressure container 2 or in a central dome, onto the external surfaces of the instruments 4 in order to clean them. The cleaning water can thereby be passed through the instruments 4 and/or the spray channels of the instruments 4 and/or, for external cleaning, through the spray nozzles of the process chamber 3.

Heating of the wash medium can take place while it is being circulated, so that the surfaces to be cleaned are first cleaned with cold wash medium. The cleaning agent can be introduced into the process chamber 3 in the form of powder or in tablet form or it can be metered in from a corresponding storage container. The wash medium can consist of surfactants or phosphates and have a pH value above 10. In order to complete the washing operation, the water is discharged from the pressure container 2.

b) Clear Rinsing—Neutralization

In a subsequent step, the water is then passed from the storage container into the process chamber 3 and heated to approximately from 45° C. to 60° C. During circulation of the water, clear rinse or neutralizer is metered in from a further storage container. Alternatively, owing to the higher temperature in comparison with step a), a second component of a cleaning tablet can also be dissolved. The liquid is in turn passed in parallel or with a time shift, that is to say intermittently, through the instruments 4 and the spray channels or is directed at the external surfaces of the instruments 4 via the spray nozzles. As clear rinse or neutralizer there are used in particular phosphoric acid esters having a pH value of from 3 to 5.

The liquid can again be discharged from the pressure container into the drainage system, or it remains in the container in order, in the subsequent maintenance operation, to take up excess maintenance agent emerging from the instruments 4 or in order briefly to rinse the oily external surfaces of the instruments with warm liquid. In this case, the liquid is not discharged until after the maintenance operation, and it may be expedient to subject the instruments 4 to compressed air in order to prevent the ingress of spray water into the interior of the instruments 4.

c) Maintenance

In a third step, maintenance agent is passed from a maintenance agent storage container into the interior of the instruments, so that the gears and bearings are lubricated. The maintenance agent can be injected in liquid form as oil or from a pressurized dispenser into a compressed air jet. It is also possible to foam the oil via the propellant contained in the pressurized dispenser and to fill the interior of the instruments with the oil/air foam. In this case, the air bubbles collapse comparatively quickly, so that the oil forms a uniform thin oil film in the whole of the instrument interior. As lubricants there are used biodegradable fatty acid ester oil/ white oil mixtures.

d) Rinsing

After the maintenance operation described above, the instruments can be rinsed on the external surface with the clear rinse liquid that is still present in the container. Alternatively, fresh water is fed from the storage container to the process chamber 3 via a pump and is directed at the external surfaces of the instruments via the spray nozzles.

e) Sterilization—Prevacuum

In order to sterilize the instruments, fresh water is fed to the process chamber 3 from the storage container. In the process chamber 3, a vacuum device is connected for ventilation, the pressure inside the process chamber 3 being monitored or recorded.

By means of the vacuum device, the air is evacuated from the process chamber 3. The vacuum is reduced by heating the water to atmospheric pressure via heating elements. The process chamber 3 is then filled with steam, it being possible for this procedure to be repeated several times, depending on the sterilization programme.

The volume of water evaporated off can be made up at each vacuum cycle or, as an alternative, all the water required for the steam generation can be introduced into the process chamber 3 right at the start of the sterilization cycle.

Alternatively to the generation of steam via heating elements located in the process chamber 3, steam for pressure equalization during ventilation or for sterilization can also be supplied from a steam pressure vessel located outside the process chamber 3.

f) Drying and Cooling

When sterilization is complete, the instruments 4 are dried by causing the steam in the process chamber 3 to condense. This is achieved by cooling the container wall or elements located in the container, for example by passing through them water taken from the storage container. The water can be supplied continuously or intermittently. When the cooling operation is complete, the water is discharged. Because the temperature inside the chamber 3 is then below 50° C., the lid 6 can be opened. The conditioning cycle for the instruments 4 is thereby completed.

It is apparent from the above description that fully automatic conditioning of dental instruments is possible with the device 1. Interventions by operating personnel are not required, so that the system is very convenient. Naturally, it is also possible to deviate from the described sequence for conditioning of the instruments.

It is further apparent from the process sequence described above that different chemical substances are used in the conditioning of the instruments for cleaning, maintenance and/or disinfection. For example, a maintenance oil, a disinfectant and a cleaning agent are used in the reconditioning of the instruments, so that—as shown in FIG. 1—the device 1 would have to be coupled with at least three storage containers 51, 52, 53 for the various media.

Figure 2:
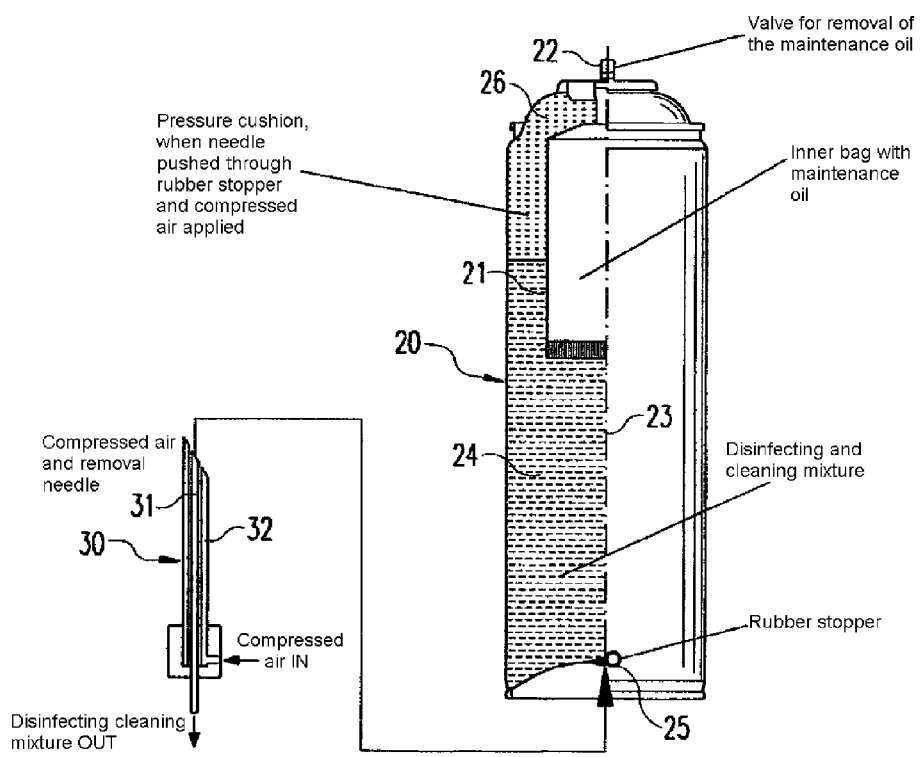
FIG. 2 shows an embodiment of a storage container according to the invention.

Because the outlay and space requirement for the attachment of corresponding storage containers is comparatively great, it is proposed according to the invention to use a novel storage container, which is to be explained hereinbelow by means of FIG. 2.

This storage container, too, is a spray can 20, but it is so configured that it provides a plurality of different media. To that end, there is arranged in the interior of the can 20 first an inner bag 21, which forms a first receiving chamber and is preferably filled with maintenance oil. The inner bag 21 is connected with a valve 22 located at the upper side of the can 20 for removal of the maintenance oil.

In the space between the bag 21 and the inside wall of the can there is further formed a second receiving region 23, in which a further medium is arranged. That medium is, for example, a mixture 24 of a cleaning agent and a disinfectant. The removal of the mixture 24 from the second receiving region 23 is also possible, a rubber stopper 25 being arranged on the underside of the can 20 for that purpose.

On insertion of the can 20 into the reconditioning device 1, the rubber stopper 25 is pierced by a needle arrangement 30, which strictly speaking consists of two needles 31 and 32 arranged concentrically to one another. The inner needle 31 serves for removal of the mixture 24 while, on the other hand, a propellant is introduced into the interior of the can 20 by way of the outer needle 32. Compressed air in particular is used as the propellant, which has the advantage that the internal pressure of the can 50 can be kept constant at a chosen value, it being possible for that chosen value to be varied within a particular pressure range. A further advantage is that, owing to the absence of flammable propellant gases, the can 50 does not constitute hazardous material, which has considerable advantages especially during transportation.

As already mentioned, the compressed air is passed through the rubber sealing stopper 25 into the inside of the can 20 by way of the outer needle 32. The pressure cushion 26 that forms thereby assists the removal both of the maintenance oil from the inner bag 21 and of the mixture from the second receiving chamber 23. The removal of the various media and the delivery of compressed air are naturally to be controlled by corresponding valves of the reconditioning device 1.

Ultimately, the invention provides the possibility of arranging a plurality of media inside a single storage container, so that handling of the system as a whole is easier. Furthermore, by reducing the number of storage containers to be attached, the risk of confusion is reduced, which brings a further increase in operational reliability.

The invention claimed is:

1. Storage container for the provision of media for disinfecting, sterilizing, and/or maintaining medical instruments, the storage container including a can comprising:
   a first receiving region formed in the can, the first receiving region adapted to contain a first medium;
   a first removal element connected with the first receiving region;
   a second receiving region formed in the can and contacting the first receiving region over at least a part of the periphery of the first receiving region, the second receiving region adapted to contain a second medium; and
   an attachment element connected with the second receiving region, the attachment element configured to remove the second medium and to deliver a propellant into the second receiving region.

2. Storage container according to claim 1, wherein the first removal element in connection with the first receiving region is a valve.

3. Storage container according to claim 1 wherein the first receiving region is a bag.

4. Storage container according to claim 1, wherein the attachment element connected with the second receiving region is a rubber stopper.

5. Storage container according to claim 1, wherein the removal element and the attachment element are arranged at two opposite ends of the can.

6. System for disinfecting, sterilizing, and/or maintaining medical instruments, having a reconditioning device for disinfecting, sterilizing and/or maintaining the instruments, which reconditioning device has attachment devices for attaching at least one storage container for media used by the device, as well as at least one storage container according to claim 1.

7. System according to claim 6, wherein the attachment devices have a first needle for removal of the second medium from the storage container.

8. System according to claim 7, wherein the attachment devices have a second needle for delivery of the propellant.

9. System according to claim 6, wherein the first and second needles are arranged concentrically.

10. System according to claim 1, wherein compressed air is used as the propellant.

* * * * *